US00PP31862P3

(12) United States Plant Patent
Beumel et al.

(10) Patent No.: US PP31,862 P3
(45) Date of Patent: Jun. 16, 2020

(54) ***JUGLANS* ROOTSTOCK NAMED 'CLIFF CLONE'**

(50) Latin Name: ***Juglans hindsii* x *regia***
Varietal Denomination: Cliff Clone

(71) Applicants: Clifford M Beumel, Yuba City, CA (US); Matthew R Conant, Rio Oso, CA (US)

(72) Inventors: Clifford M Beumel, Yuba City, CA (US); Matthew R Conant, Rio Oso, CA (US)

( * ) Notice: Subject to any disclaimer, the term of this patent is extended or adjusted under 35 U.S.C. 154(b) by 0 days.

(21) Appl. No.: 16/350,240

(22) Filed: Oct. 16, 2018

(65) Prior Publication Data

US 2020/0120841 P1 Apr. 16, 2020

(51) Int. Cl.
*A01H 5/08* (2018.01)
*A01H 6/00* (2018.01)
*A01H 5/04* (2018.01)

(52) U.S. Cl.
USPC ..... Plt./154
CPC ..... *A01H 6/00* (2018.05); *A01H 5/04* (2013.01); *A01H 5/08* (2013.01)

(58) Field of Classification Search
USPC ..... Plt./154
CPC ..... A01H 5/0825
See application file for complete search history.

*Primary Examiner* — Kent L Bell
(74) *Attorney, Agent, or Firm* — Cassandra Bright

(57) ABSTRACT

A new and distinct *Juglans* cultivar named 'Cliff Clone' is disclosed, characterized by an increased propensity to thrive in sandy soils which have been replanted into walnut. Trees grown on the new rootstock variety have shown significantly better vigor as well as increased walnut production when planted in the presence of the pathogen *Pratylenchus vulnus* and in soil known to have walnut replant disorder. The new variety is a *Juglans hindsii* x *regia*, for use as a commercial rootstock for grafting or budding onto.

5 Drawing Sheets

Latin name of the genus and species: *Juglans hindsii* x *regia*.

Variety denomination: 'Cliff Clone'.

BACKGROUND OF THE INVENTION

The new cultivar is a product of selection made by the inventors. The new variety was discovered in Rio Oso, Calif. as an individual seedling of unknown parentage, tree demonstrating superior vigor and growth in an orchard with less than ideal cultural conditions. The orchard was composed of seedling rootstocks of *Juglans hindsii* x *regia* with the variety 'Tulare', U.S. Plant Pat. No. 8,268, grafted on the top. This tree with outstanding growth was selected and observed during May of 2011.

Asexual reproduction of the new cultivar 'Cliff Clone' was first performed via tissue culture in a commercial laboratory in Yuba City, Calif. during June of 2014. Subsequent propagation has shown that the unique features of this cultivar are stable and reproduced true to type on successive generations.

Commercial walnut production is a significant and important crop in some regions, and especially in California. A significant challenge to the industry is reduced vigor of trees when planted into orchards where walnut trees have previously been planted. "Replant disorder" is characterized as a complex of fungi, bacteria, and nematodes remaining at damaging levels in the soil after the removal of the previous orchard, preventing new walnut trees from growing in a normal fashion. Developing a rootstock which can impart vigor into "replant" orchards represents a valuable and distinct improvement.

A further identified challenge in the production of commercial walnut trees is *Pratylenchus vulnus*, the primary nematode responsible for damage to commercial walnut production in California. This damage includes lack of vigor, and marked inconsistent, non-uniform growth. In modern orchard systems, a predictable and uniform tree performance is of high commercial value.

SUMMARY OF THE INVENTION

The cultivar 'Cliff Clone' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'Cliff Clone'. These characteristics in combination distinguish 'Cliff Clone' as a new and distinct *Juglans* cultivar:

1. The rootstock has shown an increased propensity to thrive in sandy soils which have been replanted into walnut. At these sites other walnut rootstocks have shown marginal success, at best, and many have succumbed to predation associated with nematodes and replant disorder.
2. In clay-loam soils, the rootstock imparts vigor comparable to the most vigorous hybrid walnut rootstock.
3. Imparts vigor and tree health to a scion of a commercial *Juglans regia* (English Walnut) in the presence of root lesion nematode *Pratylenchus vulnus* and in a replanted orchard site after the removal of a previous walnut orchard that is not displayed by currently used clonal walnut rootstocks 'VX211' (U.S. Plant Pat. No. 21,179), 'RX1' (U.S. Plant Pat. No. 20,649), or 'Vlach' (unpatented).

PARENT COMPARISON

Plants of the new cultivar 'Cliff Clone' are similar to plants of the seed parent, an unpatented, unnamed *Juglans hindsii* in most horticultural characteristics. Plants of the new cultivar 'Cliff Clone', however, differ in the following:

1. Plants of the new cultivar grow significantly more vigorously.
2. Leaves of the new variety are shorter, with fewer leaflets per leaf.
3. Leaflets of the new variety are broader with a less acute apex.

Plants of the new cultivar 'Cliff Clone' are similar to plants of the pollen parent, an unpatented, unnamed *Juglans regia* in most horticultural characteristics. Plants of the new cultivar 'Cliff Clone', however, differ in the following:

1. Plants of the new cultivar grow significantly more vigorously.
2. Leaves of the new variety are shorter, with fewer leaflets per leaf.
3. Leaflets of the new variety are broader with a less acute apex.

COMMERCIAL COMPARISON

Plants of the new cultivar 'Cliff Clone' are similar to plants of the known commercial variety 'VX211', U.S. Plant Pat. No. 21,179, in most horticultural characteristics, however, plants of the new cultivar 'Cliff Clone' differ in exhibiting superior growth and performance when directly compared to 'VX211' grown in adverse soil conditions. Confidential and controlled testing has been performed in an orchard confirmed to be infected with "replant disorder" as well as a confirmed high population of *Pratylenchus vulnus*. Scions of the commercial variety 'Chandler', U.S. Plant Pat. No. 4,388, were grafted onto both 'Cliff Clone' and 'VX211', side by side testing produced the following results:

1. Trees produced with a graft onto 'Cliff Clone' grew larger. Superior growth, including more vigorous tree growth and more uniform growth.
2. Trees produced with a graft onto 'Cliff Clone' grew much more uniformly.
3. Trees produced with a graft onto 'Cliff Clone' exhibited overall better visual health, including healthier foliage.
4. There was an increased crop yield of commercial walnut production on trees grafted onto 'Cliff Clone'.

Plants of the new cultivar 'Cliff Clone' are similar to plants of the known commercial variety 'RX1', U.S. Plant Pat. No. 20,649, in most horticultural characteristics, however, plants of the new cultivar 'Cliff Clone' differ in exhibiting superior growth and performance when directly compared to 'RX1' grown in adverse soil conditions. Confidential and controlled testing has been performed in an orchard confirmed to be infected with "replant disorder" as well as a confirmed high population of *Pratylenchus vulnus*. Scions of the commercial variety 'Chandler' were grafted onto both 'Cliff Clone' and 'RX1', side by side testing produced the following results:

1. Trees produced with a graft onto 'Cliff Clone' grew larger. Superior growth, including more vigorous tree growth and more uniform growth.
2. Trees produced with a graft onto 'Cliff Clone' grew much more uniformly.
3. Trees produced with a graft onto 'Cliff Clone' exhibited overall better health, including healthier foliage.
4. There was an increased crop yield of commercial walnut production on trees grafted onto 'Cliff Clone'.

BRIEF DESCRIPTION OF THE PHOTOGRAPHS

The accompanying photographs in FIG. 1 through FIG. 5 illustrate in full color typical plants of 'Cliff Clone' grown in a greenhouse in Yuba City, Calif. The photographs were taken using conventional techniques and equipment. While the colors in these photographs may display variances of color as compared to the living cultivar, due to LRV (light reflectance value), they are as accurate as possible using conventional photographic techniques. Colors in the photographs may appear to differ slightly from the color values cited in the botanical description, which accurately describe the colors of the new *Juglans* plant. No artificial light, photoperiodic treatments or chemical treatments were given to the plants.

Figure 1:
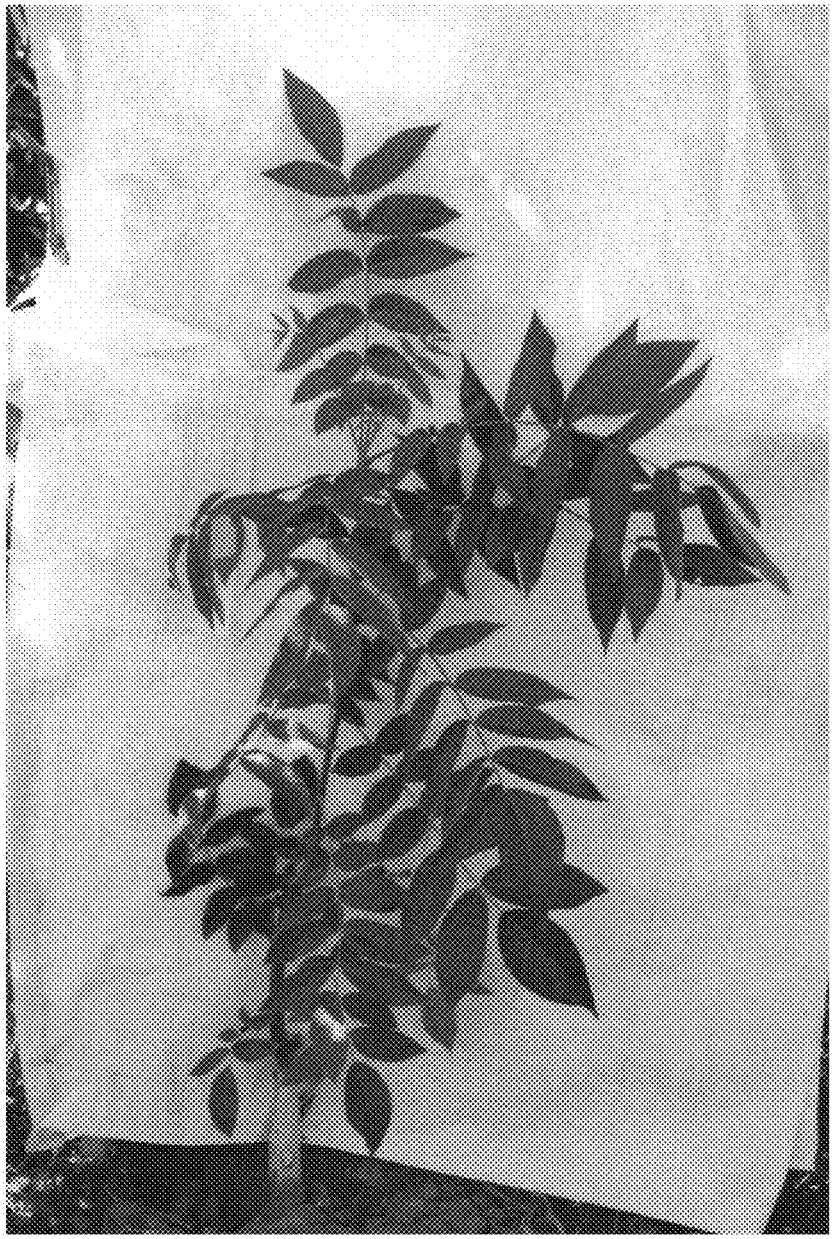
FIG. 1 illustrates in full color an un-grafted young tree at approximately 9 months of age.
Figure 2:
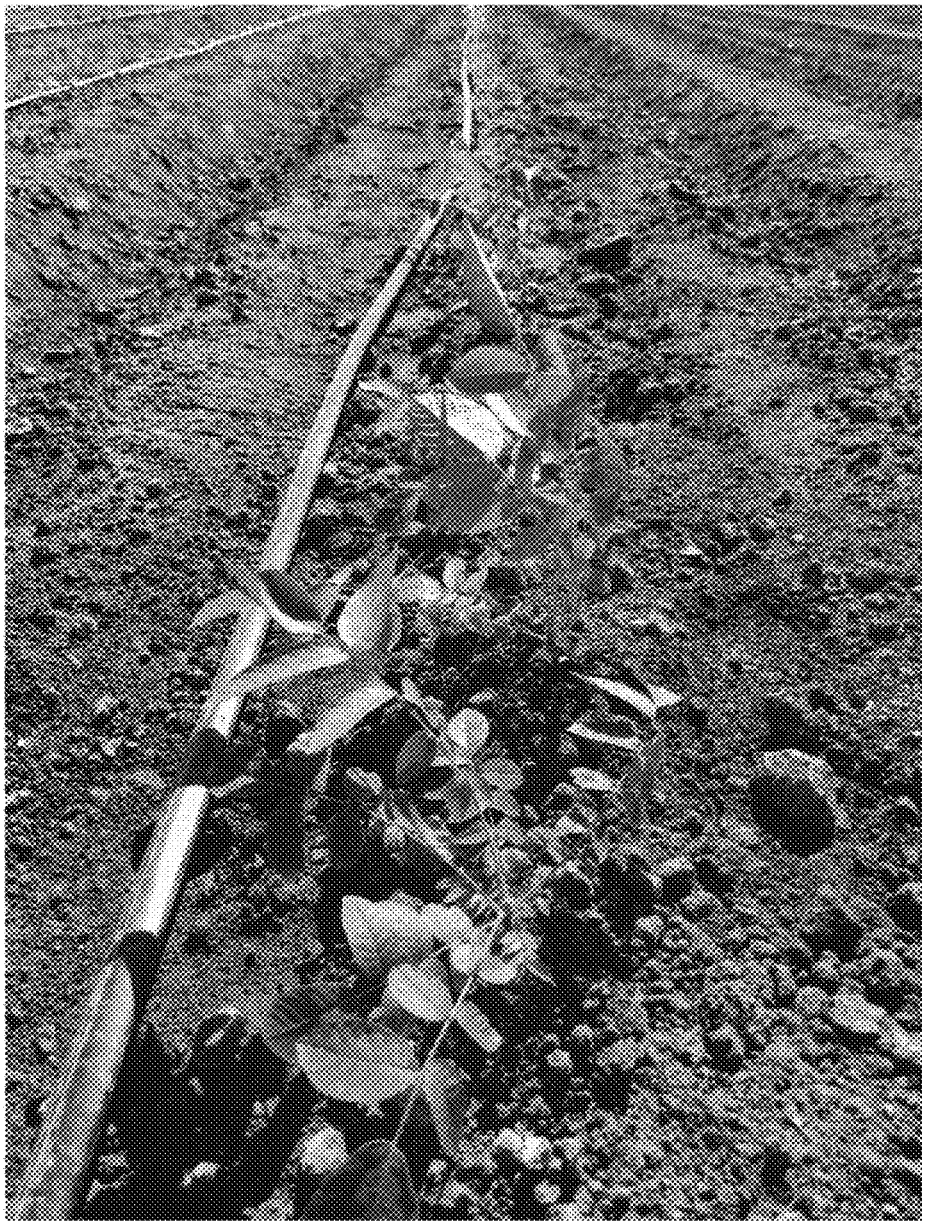
FIG. 2 illustrates in full color newly planted rootstock plugs.
Figure 3:
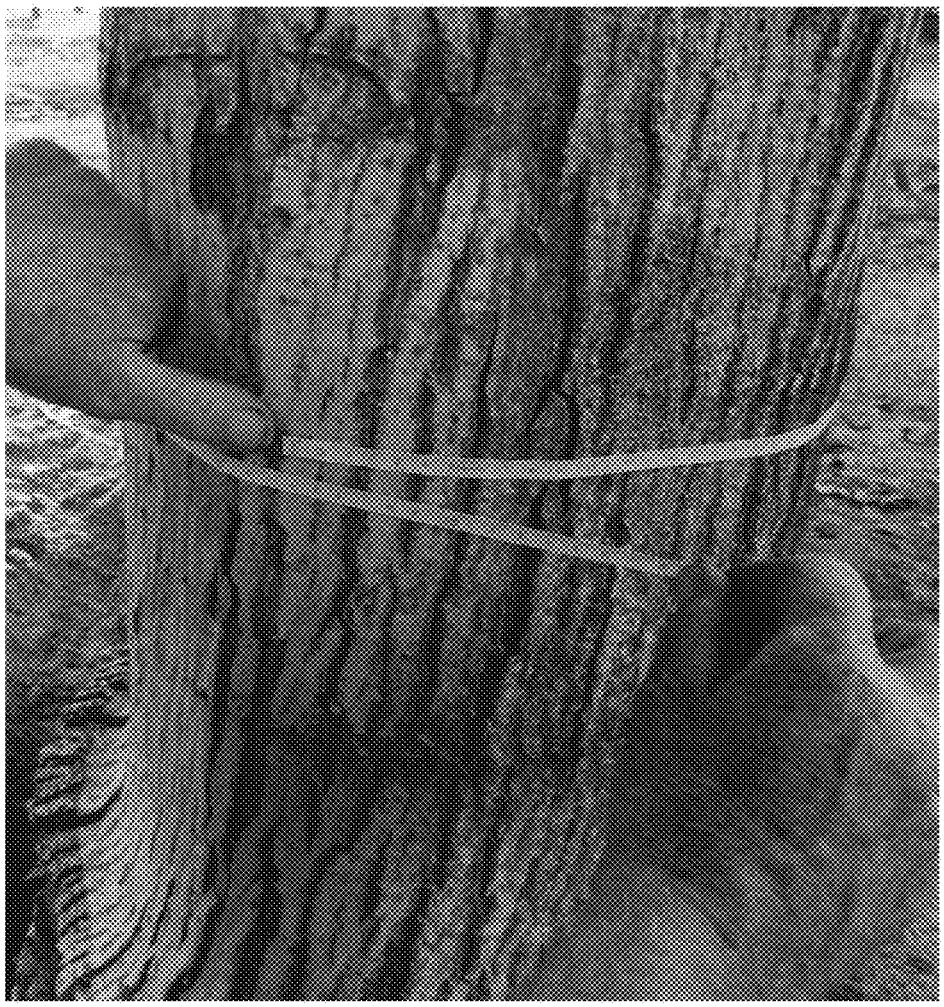
FIG. 3 illustrates in full color the trunk of a mature tree.
Figure 4:
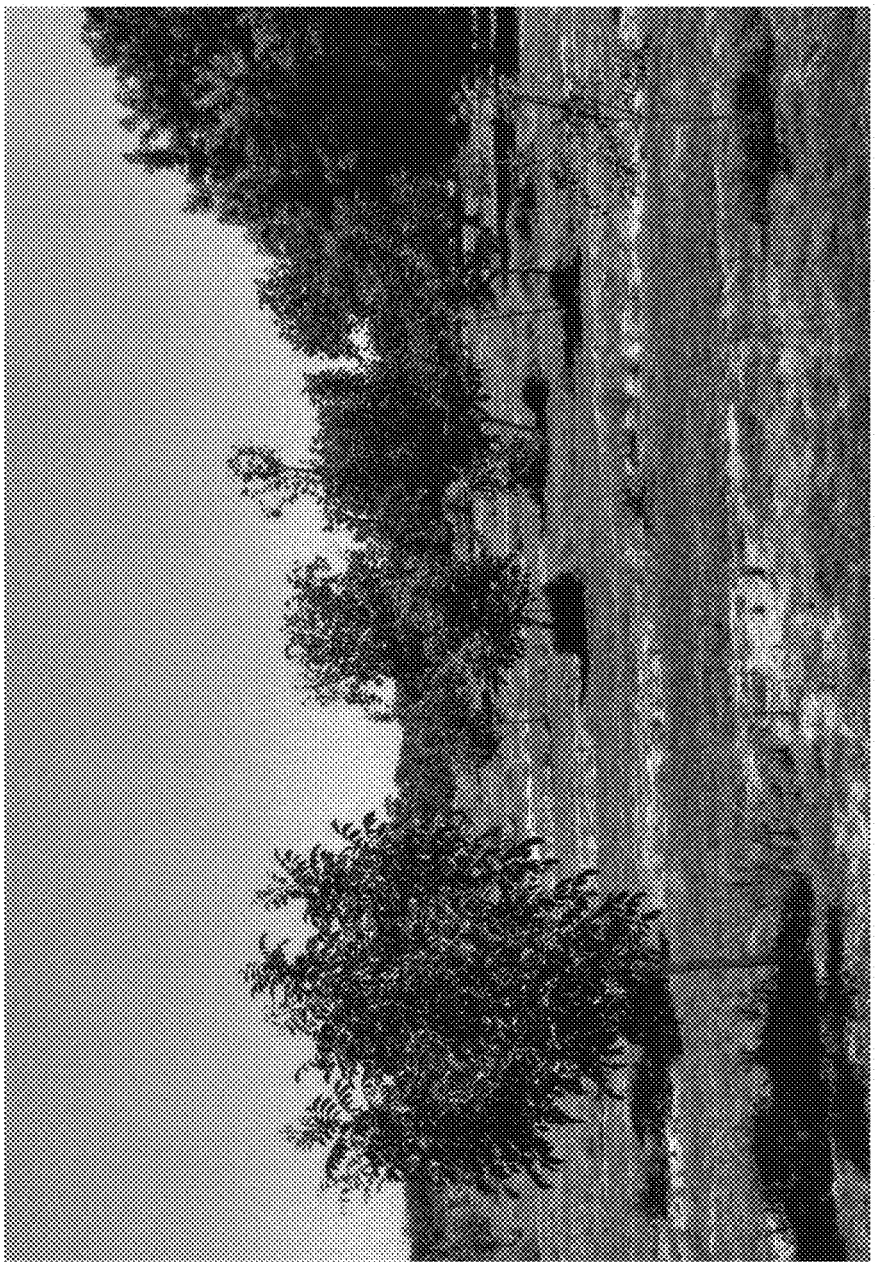

FIG. 4 illustrates in full color a comparison trial. The larger tree on the left side of the figure is 'Chandler' grafted onto 'Cliff Clone' rootstock. The tree in the same row, on the right side of the figure is 'Chandler' grafted onto 'VX211' rootstock. Age of both trees is 30 months.

Figure 5:
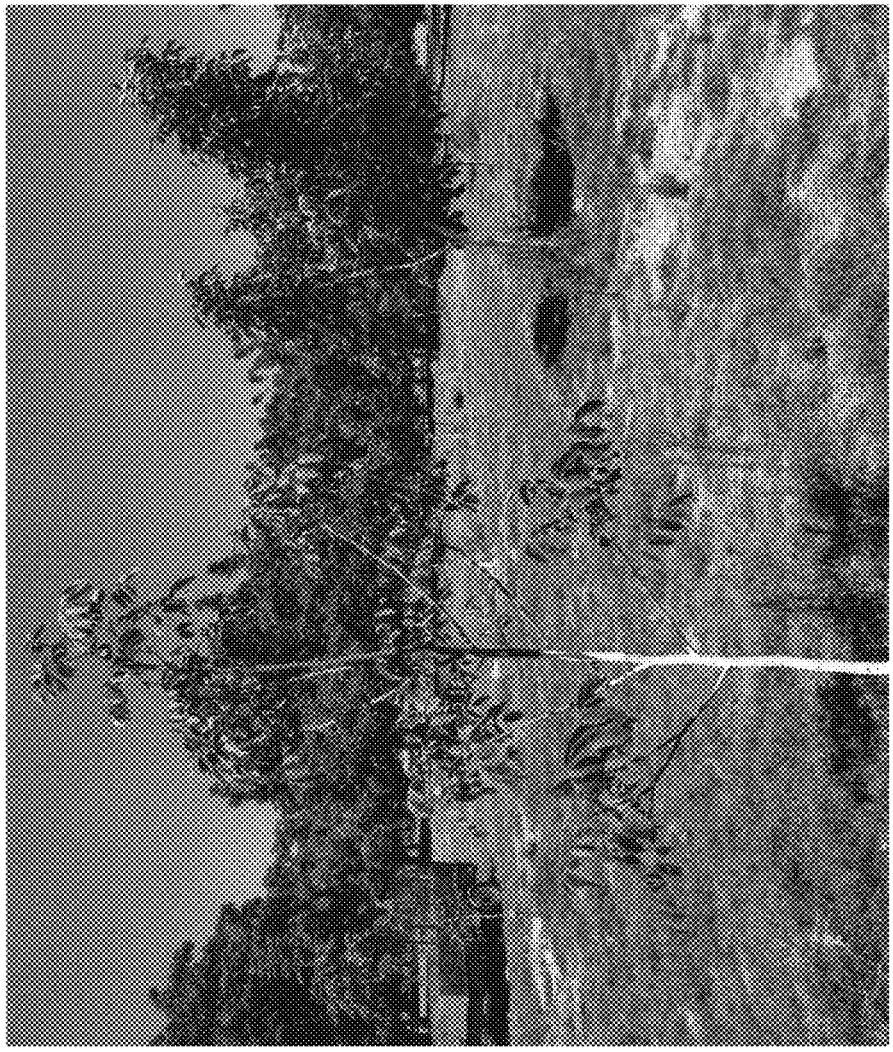

FIG. 5 illustrates in full color a different view of the same comparison trial. The larger tree on the right side of the figure is 'Chandler' grafted onto 'Cliff Clone' rootstock. The tree in the same row, on the left side of the figure is 'Chandler' grafted onto 'VX211' rootstock. Age of both trees is 30 months.

DETAILED BOTANICAL DESCRIPTION

In the following description, color references are made to The Royal Horticultural Society Colour Chart 2007 except where general terms of ordinary dictionary significance are used. The following observations and measurements describe 'Cliff Clone' plants grown outdoors in Yuba City, Calif. Growing conditions are similar to USDA Zone 9. Temperatures ranged from approximately 15 to 30 degrees C. during the day and 10 to 19 degrees C. at night. Measurements were taken from trees of various age, including 6 month old plugs, rootstock only plants of 5 months and a mature tree of 21 years. Age of the plant used is specified when measurements are given. Measurements and numerical values represent averages of typical plant types at corresponding age of maturity.

Botanical classification: *Juglans hindsii* x *regia* 'Cliff Clone'.

PROPAGATION

Time to initiate roots: About 21 days at approximately 27° C.

Root description (color, woody, fibrous, branching characteristics): Roots are fibrous and somewhat branched. Newly formed roots are delicate and fleshy, 1 to 2 mm in diameter. Mature roots are woody and more rigid.

Propagation method: In-vitro propagation has been successful.

Grafting information: Whip and tongue grafting have been found to have comparable success as with other walnut rootstocks.

PLANT

Time of year measurements taken: September.

Height: Approximately 100 cm at one year.

Plant spread: Approximately 56 cm at one year.

Typical mature height: Grafted trees can reach a height of 15 meters or more.

Typical mature spread: Grafted trees can attain a spread 10 meters or more.

Overall tree shape: Oval to Pyramidal.

Growth rate: Vigorous. Among the most vigorous walnut hybrid rootstocks.

Growth habit: Upright, large deciduous tree.

Branching characteristics: Not typically grown for above ground characteristics. To date trees have not been grown to allow typical branching. Sucker type branches emerge from trunk, which are propagated.

Trunk:

*Diameter*.—Approximately 5.2 cm at 1 year.

*Texture*.—Smooth.

*Color*.—Near Yellow-Green 148A, at about 1 year.

*Lenticels*.—Density: Approximately 8 per $cm^2$. Lenticel width: Approximately 0.08 cm. Lenticel color: Near RHS Greyed-Yellow 162D.

FOLIAGE

Leaf:

*Arrangement*.—Alternate occurring compound leaves.

*Compound leaf length*.—Average 39 cm.

*Compound leaf width*.—Average 20 cm.

*Leaflets*.—Shape: Oblanceolate. Quantity: Typically 11 or 13. Occurring in opposite pairs, with a single terminal leaflet. Average Overall Length: 9.3 cm. Average Overall Width: 3.6 cm. Attachment: Petiolate. Apex: Acute to nearly acuminate. Base: Rounded to rounded-oblique. Margin: Slightly dentate. Texture of top surface: Smooth, veins not prominent. Texture of bottom surface: Glabrous, mid-rib densely canescent. Angle of attachment: Leaves are held at an angle approximately 10 to 25 degrees from perpendicular. Leaf internode length: Approximately 5.3 cm. Typical leaf fall date: 15 November at 40° latitude, 50 meters elevation above mean sea level. Typical leaf emergence date: 20 March at 40° latitude, 50 meters elevation above mean sea level.

*Color*.—Young foliage upper side: Near RHS Green 137B. Young foliage under side: Near RHS Yellow-Green 146B. Mature foliage upper side: Near RHS Yellow-Green 147A. Mature foliage under side: Near RHS Yellow-Green 146B. Fall foliage upper side: Near RHS Yellow 2B. Fall foliage under side: Near RHS Yellow 2C.

*Venation*.—Type: Pinnate. Venation color: Upper Surface: Near RHS Yellow-Green 152D. Lower Surface: Near RHS Yellow-Green 146D.

Petiole:

*Length*.—Approximately 30 cm.

*Diameter*.—Approximately 0.35 cm.

*Color*.—Near RHS Yellow-Green 146C.

*Texture*.—Smooth.

Leaflet petiole:

*Length*.—0.5 mm.

*Diameter*.—Approximately 0.15 cm.

*Color*.—Near RHS Yellow-Green 152C.

*Texture*.—Smooth, glabrous.

FLOWER

Flowering not observed to date.

REPRODUCTIVE ORGANS

Not observed to date.

OTHER CHARACTERISTICS

Seeds and fruits: Not observed to date.

Disease resistance: Appears to adequately tolerate Replant disease more than other walnut rootstocks, known to the inventor, exhibiting equivalent or better growth than other walnut rootstocks known to the inventor. Grows as good or better than other walnut rootstocks known to the inventor in the presence of Lesion Nematode, *Pratylenchus vulnus*.

Temperature tolerance: Low temperature tolerance to approximately −9° C. Tolerates high temperature to at least 46° C.

Drought tolerance: Based on growth and graft success performance in extremely sandy soils, drought resistance appears slightly superior to other walnut hybrid rootstocks.

What is claimed is:

1. A new and distinct cultivar of *Juglans* tree named 'Cliff Clone' as herein illustrated and described.

* * * * *